United States Patent
Okumura et al.

(10) Patent No.: US 11,318,216 B2
(45) Date of Patent: May 3, 2022

(54) METHOD FOR PRODUCING RADIOHALOGEN-LABELED COMPOUND AND METHOD FOR PRODUCING RADIOPHARMACEUTICAL

(71) Applicant: NIHON MEDI-PHYSICS CO., LTD., Tokyo (JP)

(72) Inventors: Yuki Okumura, Tokyo (JP); Daisaku Nakamura, Tokyo (JP); Masato Kiriu, Tokyo (JP); Hiroaki Ichikawa, Tokyo (JP); Gota Tonoya, Tokyo (JP); Naomi Sugimoto, Tokyo (JP)

(73) Assignee: NIHON MEDI-PHYSICS CO., LTD., Tokyo (JP)

( * ) Notice: Subject to any disclaimer, the term of this patent is extended or adjusted under 35 U.S.C. 154(b) by 136 days.

(21) Appl. No.: 16/625,822

(22) PCT Filed: May 28, 2018

(86) PCT No.: PCT/JP2018/020403
§ 371 (c)(1),
(2) Date: Dec. 23, 2019

(87) PCT Pub. No.: WO2018/235535
PCT Pub. Date: Dec. 27, 2018

(65) Prior Publication Data
US 2020/0121811 A1    Apr. 23, 2020

(30) Foreign Application Priority Data
Jun. 23, 2017  (JP) .............................. JP2017-122981

(51) Int. Cl.
| A61K 51/00 | (2006.01) |
| A61M 36/14 | (2006.01) |
| A61K 51/04 | (2006.01) |
| C07B 59/00 | (2006.01) |

(52) U.S. Cl.
CPC .............. *A61K 51/04* (2013.01); *C07B 59/00* (2013.01)

(58) Field of Classification Search
CPC ................................ A61K 51/04; C07B 59/00
USPC ....................................................... 424/1.65
See application file for complete search history.

(56) References Cited

U.S. PATENT DOCUMENTS

| 9,428,497 B2 | 8/2016 | Smits et al. |
| 2008/0076914 A1* | 3/2008 | Grigg ................. A61K 51/0491 536/50 |
| 2014/0364620 A1 | 12/2014 | Nakata et al. |
| 2015/0175553 A1 | 6/2015 | Wouters et al. |
| 2017/0066748 A1 | 3/2017 | Toyama et al. |
| 2017/0158668 A1 | 6/2017 | Izawa et al. |

FOREIGN PATENT DOCUMENTS

| JP | 2008515793 A | 5/2008 |
| JP | 2015504443 A | 2/2015 |
| JP | 2015081242 A | 4/2015 |
| JP | 2017052713 A | 3/2017 |
| JP | 2017081847 A | 5/2017 |
| WO | 2006037950 A1 | 4/2006 |
| WO | 2009127372 A1 | 10/2009 |
| WO | 2011006610 A1 | 1/2011 |
| WO | 2013042668 A1 | 3/2013 |
| WO | 2015/143019 A2 | 9/2015 |
| WO | 2015/143019 A3 | 9/2015 |
| WO | 2015199205 A1 | 12/2015 |
| WO | 2017071980 A1 | 5/2017 |

OTHER PUBLICATIONS

Knott et al. J. Label. Compd Radiopharm. 2011, 54, 749-753. (Year: 2011).*
Lee et al. J. Label. Compd. Radiopharm. 2013, 56, 731-735. (Year: 2013).*
McConathy et al. Mol. Imaging 2010, 9, 329-342. (Year: 2010).*
Kostikov et al., "Oxalic Acid Supported Si -18F-Radiofluorination: One-Step Radiosynthesis of N-Succinimidyl 3-(Di-tert-butyl[18F]fluorosilyl) benzoate ([18F]SiFB) for Protein Labeling", Bioconjugate Chemistry, American Chemical Society, Dec. 8, 2011, vol. 23, No. 2, pp. 106-114.
Extended European Search Report dated Mar. 16, 2020, by the European Patent Office in corresponding European Patent Application No. 18820897.9. (8 pages).
International Search Report (with English Translation) and Written Opinion issued in corresponding International Patent Application No. PCT/JP2018/020403, 10 pages (dated Jul. 17, 2018).
English Translation of the Written Opinion of the International Searching Authority dated Jul. 17, 2018, by the Japanese Patent Office in corresponding International Patent Application No. PCT/JP2018/020403. (6 pages).

* cited by examiner

*Primary Examiner* — Michael G. Hartley
*Assistant Examiner* — Sean R Donohue
(74) *Attorney, Agent, or Firm* — Buchanan Ingersoll & Rooney PC

(57) ABSTRACT

Provided is a method for producing a radiohalogen-labeled compound, the method comprises: a step in which a radiohalogen-labeling precursor compound (S-L) having a leaving group (L) capable of being nucleophilically substituted by a radioactive halide ion ($X^-$) is subjected to a radiohalogenation reaction to obtain a reaction mixture RM1 which contains the radiohalogen-labeling precursor compound (S-L) and a reaction product (S—X) resulting from the radiohalogenation reaction; a step in which the reaction mixture RM1 is mixed with a polyvalent acid or a salt thereof to obtain a reaction mixture RM2; and a step in which the reaction product (S—X) is purified from the reaction mixture RM2 by a solid phase extraction method.

4 Claims, No Drawings

METHOD FOR PRODUCING RADIOHALOGEN-LABELED COMPOUND AND METHOD FOR PRODUCING RADIOPHARMACEUTICAL

TECHNICAL FIELD

The present invention relates to a method for producing a radiohalogen-labeled compound and a method for producing a radiopharmaceutical.

BACKGROUND ART

Usually, at the preparation of a radiohalogenated drug, a compound in which a leaving group is bound to a site to be halogen-labeled of a target substrate is prepared as a labeling precursor compound, and a nucleophilic substitution reaction is carried out by reacting the labeling precursor compound with a radioactive halide ion in many cases. This reaction is generally performed using a small amount of radioactive halide ions for a large amount of labeling precursor compounds. Therefore, purification of the obtained radiohalogen-labeled compound is generally performed by separating a large amount of unreacted labeling precursor compounds by a high performance liquid chromatography method (HPLC method). However, the HPLC method is complicated and time-consuming, and in consideration of decay of radiohalogen, it causes a decrease in the yield of target compounds.

As an alternative strategy that does not require HPLC purification, Patent Literature 1 proposes that a compound in which a part of the leaving group of the above labeling precursor compound is modified with a compound M (purification moiety) is prepared as a labeling precursor compound, and this compound is reacted with a nucleophile, such as a radioactive halide ion, so that the species containing the purification moiety M can be easily separated from other species that do not contain the purification moiety M.

Patent Literatures 2 and 3 propose a radiohalogen-labeling precursor compound with a leaving group having a lipophilic functional group introduced therein and a radiohalogen labeling method.

CITATION LIST

Patent Literature

Patent Literature 1: WO 2009/127372 A
Patent Literature 2: WO 2011/006610 A
Patent Literature 3: JP 2017-52713 A

SUMMARY OF INVENTION

The method disclosed in Patent Literature 1 is based on the concept that after the radiohalogenation reaction, the active group fixed to the resin is allowed to chemically react with the purification moiety M of the labeling precursor compound. Therefore, there are problems such as adversely affecting the yield of the radiohalogenation reaction product and requiring preparation of the resin such as introducing a special active group.

In addition, the methods disclosed in Patent Literatures 2 and 3 require changing a design of the structure of an existing labeling precursor compound.

The present invention has been made in view of the above circumstances, and an object thereof is to provide a technique for separating and purifying a reaction product of radiohalogenation reaction from an unreacted radiohalogen-labeling precursor compound without changing the design of the structure of the labeling precursor compound but with a method that does not depend on the HPLC method.

An aspect of the present invention provides
a method for producing a radiohalogen-labeled compound, the method including:
a step of performing a radiohalogenation reaction on a radiohalogen-labeling precursor compound having a leaving group capable of being nucleophilically substituted by a radioactive halide ion for obtaining a first reaction mixture containing the radiohalogen-labeling precursor compound and a reaction product of the radiohalogenation reaction;
a step of mixing the above first reaction mixture with a polyvalent acid or a salt thereof for obtaining a second reaction mixture; and
a step of purifying the above reaction product from the above second reaction mixture by a solid phase extraction method.

Another aspect of the present invention provides a method for producing a radiopharmaceutical containing a radiohalogen-labeled compound as an active ingredient, the method including carrying out the above-mentioned method for producing a radiohalogen-labeled compound.

According to the present invention, it is possible to separate and purify a reaction product of the radiohalogenation reaction from an unreacted radiohalogen-labeling precursor compound without changing the design of the structure of the labeling precursor compound but with a method that does not depend on a HPLC method.

Further, in the methods disclosed in Patent Literatures 2 and 3, since a difference in fat solubility between the radiohalogen-labeling precursor compound and the radiohalogen-labeled compound is increased, in a case where non-radioactive impurities in the radiopharmaceutical containing the radiohalogen-labeled compound as an active ingredient are analyzed in a reverse phase system, there is a concern that the analysis needs time, and as a result, the time required for the quality test of the radiopharmaceutical is increased. However, since the method of the present invention does not design the radiohalogen-labeling precursor compound that increases the fat solubility difference between the radiohalogen-labeling precursor compound and the radiohalogen-labeled compound, it is possible to shorten the synthesis time of the radiopharmaceutical without extending the time required for the quality test of the radiopharmaceutical, and to shorten the production time of the radiopharmaceutical as a whole.

DESCRIPTION OF EMBODIMENTS

In a method for producing a radiohalogen-labeled compound of the present invention, the following steps, Step 1 to Step 3 are sequentially performed.
Step 1: A step of obtaining a reaction mixture RM1 (first reaction mixture) containing a radiohalogen-labeling precursor compound (S-L) and a reaction product (S—X) of a radiohalogenation reaction, in which the radiohalogenation reaction is performed on the radiohalogen-labeling precursor compound (S-L) having a leaving group (L) that is capable of being nucleophilically substituted by a radioactive halide ion ($X^-$).
Step 2: A step of obtaining a reaction mixture RM2 (second reaction mixture), in which the reaction mixture RM1 is mixed with a polyvalent acid (AH) or a salt thereof ($A^-B^+$).

Step 3: A step of purifying a reaction product (S—X) from the reaction mixture RM2 by a solid phase extraction method.

Step 1: Radiohalogenation Step

In the radiohalogenation step, a radiohalogenation reaction is performed on a radiohalogen-labeling precursor compound (S-L) having a leaving group (L) that is capable of being nucleophilically substituted by a radioactive halide ion ($X^-$), so as to obtain a reaction mixture RM1 containing the radiohalogen-labeling precursor compound (S-L) and a reaction product (S—X) of the radiohalogenation reaction.

Here, the "radiohalogen" is selected from the radioisotopes of fluorine, chlorine, bromine, iodine, and astatine, specifically, $^{18}F$, $^{34m}Cl$, $^{76}Br$, $^{123}I$, $^{124}I$, $^{125}I$, $^{131}I$, and $^{211}At$. Among them, radioactive fluorine ($^{18}F$) is preferable.

The radioactive halide ion ($X^-$) can be generated by a commonly used method. For example, in a case of a radioactive fluoride ion, it can be generated from [$^{18}O$] water by $^{18}O$ (p, n)$^{18}F$ reaction with a cyclotron.

Further, the radioactive halide ion ($X^-$) may include a counter ion. For example, in the case of the radioactive fluoride ion, an alkali metal ion or a tetraalkylammonium ion can be used as the counter ion. Here, examples of the alkali metal ion include a lithium ion, a sodium ion, a potassium ion, a rubidium ion, and a cesium ion. Examples of the tetraalkylammonium ion include a tetramethylammonium ion, a tetraethylammonium ion, a tetrapropylammonium ion, and a tetrabutylammonium ion. An anion exchange resin can be used for the preparation of the radioactive halide ion ($X^-$) with the desired counter ion. As an example, it can be prepared by passing [$^{18}O$] water containing the radioactive fluoride ion through the anion exchange resin prepared in a carbonate type or bicarbonate type to adsorb the radioactive fluoride ion, and eluting the radioactive fluoride ion with a potassium carbonate aqueous solution or a tetraethylammonium bicarbonate aqueous solution.

The radioactive halide ion ($X^-$) may be activated using a phase transfer catalyst. Examples of the phase transfer catalyst used here include a tetraalkylammonium salt such as a tetramethylammonium salt, a tetraethylammonium salt, a tetrapropylammonium salt, and a tetrabutylammonium salt, crown ether, and cryptand. For example, in the case of the radioactive fluoride ion, it can be activated by being mixed with 4,7,13,16,21,24-hexaoxa-1,10-diazabicyclo [8.8.8] hexacosane (trade name: Kryptofix 222) or a tetraalkylammonium salt, and heated as necessary. Regarding activation of the radioactive fluoride ion, there is a method of (i) preparing an aqueous potassium radioactive-fluoride solution using an anion exchange resin and an aqueous potassium carbonate solution, then, mixing the aqueous potassium radioactive-fluoride solution with 4,7,13,16,21,24-hexaoxa-1,10-diazabicyclo [8.8.8] hexacosane (trade name: Kryptofix 222), and activating the radioactive fluoride ion and evaporating water while azeotroping with acetonitrile, or (ii) activating the radioactive fluoride ion and evaporating water while azeotroping, with acetonitrile, an aqueous tetraethylammonium radioactive-fluoride solution prepared using an anion exchange resin and a tetraethylammonium bicarbonate aqueous solution.

The leaving group (L) is not limited as long as it is left when the radioactive halide ion ($X^-$) attacks it as a nucleophile, but is preferably a sulfonyloxy group. The "sulfonyloxy group" is an aromatic sulfonyloxy group, an alkylsulfonyloxy group, or a haloalkylsulfonyloxy group. Examples of the aromatic sulfonyloxy group include a benzenesulfonyloxy group, a p-toluenesulfonyloxy group, and a p-nitrobenzenesulfonyloxy group. Examples of the alkylsulfonyloxy group include a methanesulfonyloxy group. Examples of the haloalkylsulfonyloxy group include a trifluoromethanesulfonyloxy group.

The radiohalogen-labeling precursor compound (S-L) is a compound in which the leaving group (L) is introduced to a substrate (S) consisting of a biomolecule recognition site or the like (here, the substrate (S) includes one that is protected at a group on which the radioactive halide ion ($X^-$) acts, such as a hydroxy group, an amino group, or a carboxyl group), and is exemplified by the following compounds.

Compound represented by formula (1): Labeling precursor compound of fluorodeoxyglucose ($^{18}F$)

Compound represented by formula (2): Labeling precursor compound of fluciclovine ($^{18}F$)

Compound represented by formula (3): Labeling precursor compound of [$^{18}F$]FLT (3'-[$^{18}F$] fluoro-3'-deoxythymidine)

Compound represented by formula (4): Labeling precursor compound of [$^{18}F$] FET (O-(2-[$^{18}F$] fluoroethyl)-L-tyrosine)

Compound represented by formula (5): Labeling precursor compound of [$^{18}F$] FES (6α-[$^{18}F$]fluoro-17β-estradiol)

Compound represented by formula (6): Labeling precursor compound of [$^{18}F$]FMISO ([$^{18}F$]fluoromisonidazole)

Compound represented by formula (7): Labeling precursor compound of [$^{18}F$]FRP-170 (1-(2-[$^{18}F$]fluoro-1-(hydroxymethyl) ethoxy) methyl-2-nitroimidazole)

Compound represented by formula (8): Labeling precursor compound of [$^{18}F$]FAZA ([$^{18}F$]fluoroazomycin arabinoside)

Compound represented by formula (9): Labeling precursor compound of 1-(2,2-dihydroxymethyl-3-[$^{18}F$] fluoropropyl)-2-nitroimidazole (Compound 1 of WO 2013/042668 A)

Compound represented by formula (10): Labeling precursor compound of florbetapir ($^{18}F$)

Compound represented by formula (11): Labeling precursor compound of florbetaben ($^{18}F$)

Compound represented by formula (12): Labeling precursor compound of [$^{18}F$] FP-CIT Compound represented by formula (13): Labeling precursor compound of [$^{18}F$]FDDNP (2-(1-{6-[(2-[$^{18}F$] fluoroethyl)(methyl)amino]-2-naphthyl}-ethylidene)malononitrile)

Compound represented by formula (14): Labeling precursor compound of a compound having CYP11B2 selective inhibitory activity disclosed in WO 2015/199205 A In the formula (14), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group having 1 to 10 carbon atoms, $R_4$ represents a hydrogen atom, a hydroxy group, or an alkoxy group having 1 to 10 carbon atoms, n represents an integer of 1 to 5, A represents CH or a nitrogen atom, $X_1$ and $X_3$ each independently represent a hydrogen atom or a halogen atom, $X_2$ represents a hydrogen atom, a halogen atom, or a nitrile group, at least one of $X_1$, $X_2$ and $X_3$ is a halogen atom, and $R_a$s each independently represent an alkyl group having 1 to 10 carbon atoms.

(1)

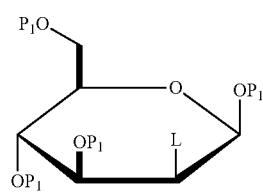

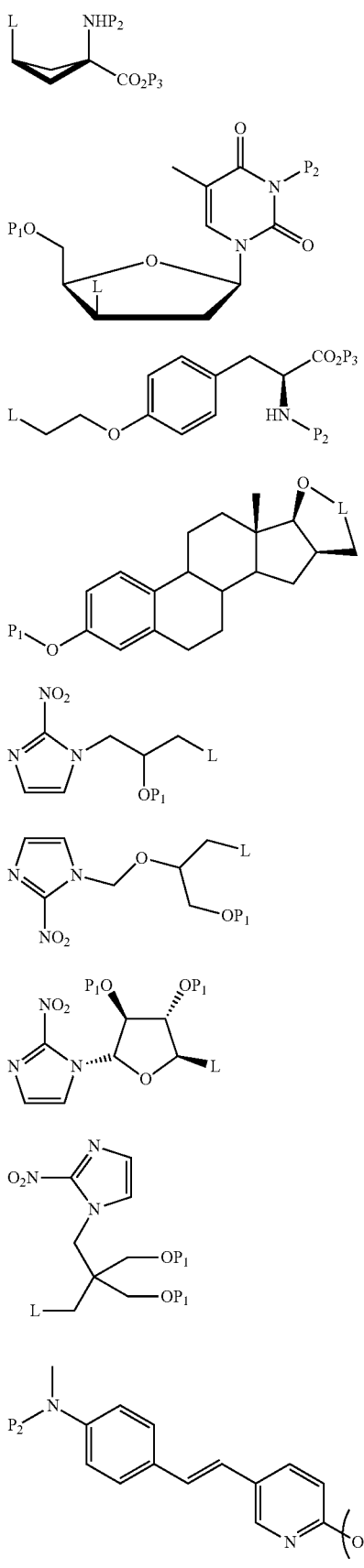
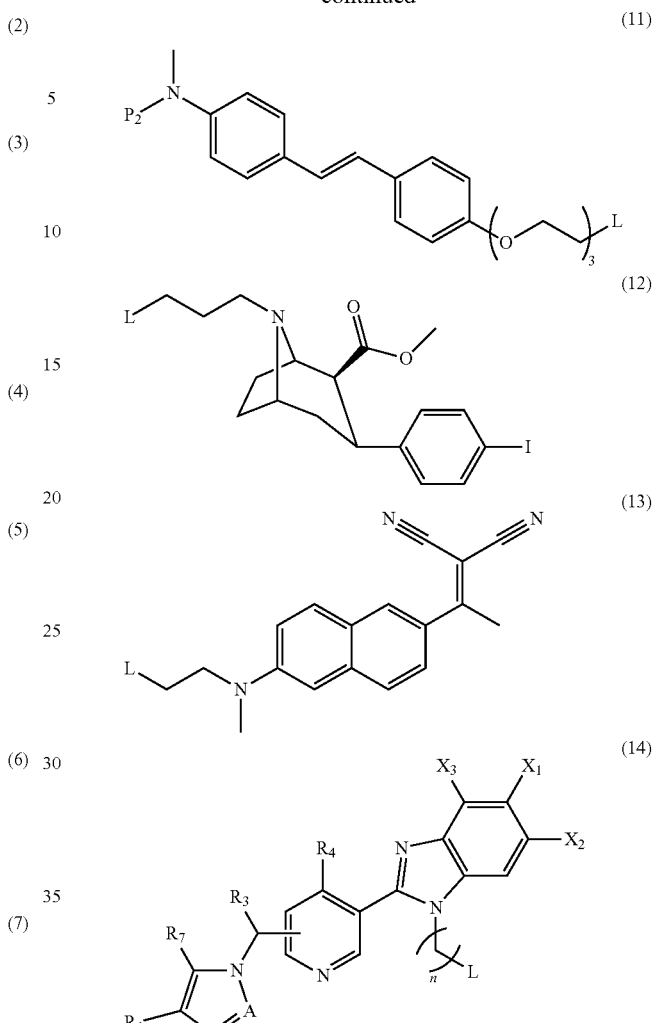

In the formulae (1) to (14), L is a leaving group, P₁ is a protective group of a hydroxy group, P₂ is a protective group of an amino group, and P₃ is a protective group of a carboxyl group. L can be individually selected from the compounds described above for each of the compounds represented by the formulae (1) to (14). $P_1$, $P_2$, and $P_3$ can be individually selected from the compounds disclosed in Greene's Protective Groups in Organic Synthesis (published by John Wiley & Sons Inc, 5th edition, published on Oct. 27, 2014) for each of the compounds represented by the formulae (1) to (14).

The radiohalogenation reaction is not particularly limited as long as the nucleophilic substitution reaction of the radiohalogen-labeling precursor compound (S-L) using the radioactive halide ion (X⁻) as a nucleophile proceeds, and known methods can be appropriately used. Preferably, it is performed by using an aprotic solvent in the presence of a base. It may be performed under heating conditions to increase the reaction rate.

Examples of the aprotic solvent include acetone, diethyl ether, dimethylformamide, dimethyl sulfoxide, and acetonitrile.

As the base, non-nucleophilic bases such as potassium carbonate, triethylamine, N,N-diisopropylethylamine, and diazabicycloundecene are preferably used.

Examples of radiofluorination reaction using a radioactive fluoride ion as the radioactive halide ion (X⁻) include a method that is performed in the presence of a phase transfer catalyst and a base. Typical examples thereof include a method of using 4,7,13,16,21,24-hexaoxa-1,10-diazabicyclo[8.8.8]hexacosane (trade name: Kryptofix 222) and potassium carbonate and a method of using a tetraalkylammonium bicarbonate such as tetramethylammonium bicarbonate, tetraethylammonium bicarbonate, tetrapropylammonium bicarbonate, and tetrabutylammonium bicarbonate. The radiofluorination reaction can be preferably performed under a temperature condition of 20° C. to 180° C.

In the radiohalogenation reaction, the amount of substance of the radiohalogen-labeling precursor compound (S-L) to be used is an excess amount relative to the amount of substance of radioactive halide ions. Therefore, the reaction mixture RM1 obtained by performing the radiohalogenation reaction contains at least the radiohalogen-labeling precursor compound (S-L) and the reaction product (S—X).

Step 2: Decomposition Step of Radiohalogen-Labeling Precursor Compound

In the decomposition step of the radiohalogen-labeling precursor compound (S-L), the reaction mixture RM1 is mixed with the polyvalent acid (AH) or a salt thereof ($A^-B^+$), and a substitution reaction between the leaving group (L) of the radiohalogen-labeling precursor compound (S-L) and the polyvalent acid ion ($A^-$) is performed to obtain a decomposition product (S-A) of the radiohalogen-labeling precursor compound. With such a configuration, it is possible to obtain the reaction mixture RM2 containing the reaction product (S—X) of the radiofluorination reaction and the decomposition product (S-A) of the radiohalogen-labeling precursor compound.

As the polyvalent acid (AH) which has a valence of 2 or more, can be appropriately used one that is capable of being substituted with the leaving group (L) of the radiohalogen-labeling precursor compound (S-L), but does not act on the reaction product (S—X). The polyvalent acid may be a polyvalent organic acid or polyvalent inorganic acid. The polyvalent organic acid has a plurality of acidic groups each of which is selected from a carboxyl group, a sulfonic acid group, and a phenol group, or a combination of these acidic groups, and examples of those having a plurality of carboxyl groups include citric acid, oxalic acid, phthalic acid, malic acid, tartaric acid, diethylenetriaminepentaacetic acid (DTPA), and ethylenediaminetetraacetic acid (EDTA). Moreover, gentisic acid exemplifies one having a combination of a carboxyl group and a phenol group. Moreover, phosphoric acid exemplifies a polyvalent inorganic acid.

The polyvalent acid may form a salt ($A^-B^+$) in order to increase the reactivity of the radiohalogen-labeling precursor compound (S-L). The polyvalent acid salt ($A^-B^+$) is a salt of a polyvalent acid ion ($A^-$) and cation ($B^+$), is preferably a salt formed of the polyvalent acid and the phase transfer catalyst, and is more preferably a salt formed of a polyvalent organic acid and a phase transfer catalyst. In a preferable example, the polyvalent acid salt ($A^-B^+$) can be prepared by mixing the polyvalent acid and the phase transfer catalyst. Examples of the phase transfer catalysts used herein include tetraalkylammonium salts such as a tetramethylammonium salt, a tetraethylammonium salt, a tetrapropylammonium salt, and a tetrabutylammonium salt, and an alkali metal complex of crown ether or cryptand (for example, a potassium ion ($K^+$) complex of 4,7,13,16,21,24-hexaoxa-1,10-diazabicyclo[8.8.8]hexacosane (trade name: Kryptofix 222)). Formation of a salt of the polyvalent acid and the phase transfer catalyst is preferably made by mixing the polyvalent acid and the phase transfer catalyst under the condition where the amount of substance of the polyvalent acid multiplied by the valence is equivalent to the amount of substance of the phase transfer catalyst. Moreover, in preparation of the salt of the polyvalent acid, the polyvalent acid and the phase transfer catalyst may be mixed together under a solvent. As the solvent, a solvent which the polyvalent acid and the phase transfer catalyst are dissolved in and can be easily evaporated can be appropriately selected, and water; alcohol such as methanol and ethyl alcohol; acetone; tetrahydrofuran; ethyl acetate and the like can be specified.

The amount of substance of the polyvalent acid or the salt thereof used in Step 2 may be theoretically required to be equivalent to the amount of substance of the radiohalogen-labeling precursor compound (S-L) remaining after the radiofluorination reaction of Step 1, and may be equivalent to the amount of substance of the radiohalogen-labeling precursor compound (S-L) used in Step 1. From the viewpoint of quickly decomposing the radiohalogen-labeling precursor compound (S-L), the polyvalent acid or the salt thereof is preferably used in an excessive amount of substance relative to the amount of substance of the radiohalogen-labeling precursor compound (S-L) used in Step 1. For example, the amount of substance of the polyvalent acid or the salt thereof relative to the amount of substance of the radiohalogen-labeling precursor compound (S-L) used in Step 1 is 1 to 100 molar equivalents, preferably 1.5 to 50 molar equivalents, and more preferably 2 to 20 molar equivalents.

The mixture of the polyvalent acid or the salt thereof and the reaction mixture RM1 may be heated as necessary to accelerate the reaction rate between the polyvalent acid ion ($A^-$) and the radiohalogen-labeling precursor compound (S-L). In addition, in a case of heating a mixture of the reaction mixture RM1 and the polyvalent acid or the salt thereof, it is preferable to heat the mixture in a solvent. As types of the solvent and temperature conditions, those that can increase the reactivity of the polyvalent acid ion ($A^-$) and that do not react with or decompose the reaction product (S—X) are selected. In a case where the radiohalogenation reaction is performed in the aprotic solvent in Step 1, the reaction mixture RM1 may be mixed with the polyvalent acid or the salt thereof in a state of containing the aprotic solvent. Further, a solvent may be added to the reaction mixture RM1, or the aprotic solvent used in the radiohalogenation reaction may be evaporated to use a solvent different from the solvent used in the radiohalogenation reaction. As the solvent used here, acetonitrile, dimethyl sulfoxide, or dimethylformamide is preferably used. The temperature condition is preferably 60° C. to 180° C.

From the viewpoint of increasing the reactivity of the polyvalent acid ion ($A^-$) with the radiohalogen-labeling precursor compound (S-L), the reaction mixture RM1 preferably contains the phase transfer catalyst used in the radiohalogenation reaction.

In the manner described above, it is possible to obtain the reaction mixture RM2 containing the reaction product (S—X) and the decomposition product (S-A) of the radiohalogen-labeling precursor compound.

Step 3 Purification Step

In the purification step, the reaction product (S—X) of the radiohalogenation reaction is purified from the reaction mixture RM2 by a solid phase extraction method.

The solid phase extraction method used in Step 3 is not particularly limited as long as it has the condition where the reaction product (S—X) of the radiohalogenation reaction and the decomposition product (S-A) of the radiohalogen-labeling precursor compound can be separated from each other, and it is preferable to use a solid phase cartridge having an anion exchange group. In this way, among the plurality of acidic groups of the polyvalent acid, acidic groups other than one acidic group bound to S (substrate) by substitution with the leaving group (L) ionically bind to anion exchange groups of the solid phase cartridge, and thus the decomposition product (S-A) can be held in the solid phase cartridge. On the other hand, since the reaction product (S—X) of the radiohalogenation reaction does not ionically bind to the anion exchange group of the solid phase cartridge, its adsorption ability to the solid phase cartridge is weak relatively to the decomposition product (S-A) of the radiohalogen-labeling precursor compound. Therefore, it is possible to separate the reaction product (S—X) of the radiohalogenation reaction from the decomposition product (S-A) of the radiohalogen-labeling precursor compound.

In addition, the solid phase extraction method used in Step 3 more preferably uses a solid phase cartridge (mixed-mode solid-phase cartridge) having both reverse-phase distribution ability and anion exchange ability. Specifically, it is preferable to use a solid phase cartridge in which an anion exchange group is bound to a porous polymer consisting of a copolymer of divinylbenzene and vinyl pyrrolidone, or a solid phase cartridge having an octadecyl group and an anion exchange group. In this way, the non-radioactive impurities and the reaction product (S—X) of the radiohalogenation reaction which are contained in the reaction mixture RM2 are separated from each other so that the purity of the reaction product (S—X) of the radiohalogenation reaction can be further improved.

Examples of the operation of the solid phase extraction method include a method performed in such a manner that the reaction mixture RM2 is diluted with water and passed through the mixed mode solid phase cartridge, then the reaction product (S—X) of the radiohalogenation reaction and the decomposition product (S-A) of the radiohalogen-labeling precursor compound are adsorbed on the solid phase cartridge, and the reaction product (S—X) is eluted with ethanol while the decomposition product (S-A) of the radiohalogen-labeling precursor compound is still adsorbed on the solid phase cartridge. However, types of the diluting solution and the eluent are not limited to this example, and various types can be adopted depending on the type of the reaction product (S—X) of the radiohalogenation reaction.

In a case where the reaction product (S—X) of the radiohalogenation reaction is a target radiohalogen-labeled compound, the target radiohalogenated compound can be obtained by performing the solid phase extraction method in Step 3. In a case where a compound having a protective group ($P_1$, $P_2$, $P_3$) as indicated in the formulae (1) to (11) is used as the radiohalogen-labeling precursor compound (S-L) in Step 1, the target radiohalogen-labeled compound can be obtained by further performing a deprotecting reaction on the reaction product (S—X) of the radiohalogenation reaction after Step 3.

In addition, after Step 3, for purification of the radiohalogen-labeled compound, purification using alumina to remove the radioactive halide ions or purification using a reverse-phase solid phase cartridge for the purpose of separation of non-radioactive impurities may be further performed.

A radiopharmaceutical can be prepared by appropriately adding a pH regulator, a solubilizer, a stabilizer, or an antioxidant to the obtained radiohalogen-labeled compound, and diluting with water or an isotonic solution such as physiological saline.

EXAMPLES

The present invention is described below in more detail with reference to examples, but the present invention is not limited to these contents.

(Example 1) Synthesis of Tetraethylammonium Citrate

Tetraethylammonium bicarbonate (15.6 mmol, 2.98 g) was dissolved in 30 ml of methanol, and citric acid (5.2 mmol, 1.0 g) was added thereto. After stirring this at room temperature for 30 minutes, the solvent was distilled off. The residue was washed three times with chloroform (20 mL) and then dried under reduced pressure to obtain tetraethylammonium citrate (5.0 mmol, 2.8 g).

NMR apparatus used: AVANCE-III (manufactured by Bruker)
$^1$H-NMR (solvent: deuterated dimethylformamide, resonance frequency: 500 MHz): δ 3.23 (q, J=7.2 Hz, 24H), 2.23 and 2.17 (qa-b, J=14.6 Hz, 4H), 1.18 (t, J=7.2 Hz, 36H).

(Example 2) Preparation of [$^{18}$F] CDP2230

Following Steps 1 to 3 below, 6-chloro-5-fluoro-1-(2-[$^{18}$F] fluoroethyl)-2-[5-(imidazol-1-ylmethyl)pyridin-3-yl]benzimidazole ([$^{18}$F] CDP2230; the compound [$^{18}$F]100 of WO 2015/199205), which is an aldosterone synthase (CYP11B2) imaging agent, was produced.

Step 1: [$^{18}$F] fluoride ion-containing [$^{18}$O] water (with the amount of radioactivity being 43.8 MBq as a value corrected at the start of synthesis) was allowed to pass through Sep-Pak Light QMA (trade name, manufactured by Nihon Waters K.K.) prepared in carbonate type to adsorb and collect [$^{18}$F] fluoride ion. Subsequently, a tetraethylammonium bicarbonate aqueous solution (5.1 µmol/L, 0.2 mL) and a solution of 0.8 mL of acetonitrile were allowed to pass through the column to elute [$^{18}$F] fluoride ion. The resulting eluent was heated under argon gas flow at 110° C. to evaporate water. Thereafter, acetonitrile (0.3 mL×3) was added thereto, and the resulting mixture was azeotropically dried and solidified. A dimethyl sulfoxide solution (1.0 mL) in which 6-chloro-5-fluoro-2-[5-(imidazol-1-ylmethyl)pyridin-3-yl]-1-[2-(p-toluenesulfonyloxy)ethyl]benzimidazole (precursor compound 1 corresponding to Compound 17 of WO 2015/199205) (5 mg, equivalent to 9.52 µmol) was dissolved was added thereto, and the resulting mixture was heated at 100° C. for 7 minutes to perform a radiofluorination reaction.

Step 2: After completion of Step 1, 55.2 mg (equivalent to 95.2 µmol) of tetraethylammonium citrate prepared in Example 1 was dissolved in 0.5 mL of dimethyl sulfoxide solution, added to the reaction solution of the radiofluorination reaction, and heated at 100° C. for 5 minutes.

Step 3: After completion of Step 2, 15 mL of injection water was added thereto, and the resulting mixture was allowed to pass through Oasis (registered trademark) WAX Plus (trade name, manufactured by Nihon Waters K.K.) to adsorb and collect [$^{18}$F] CDP2230 on the column. The column was washed with water (10 mL), and then ethanol (5 mL) was allowed to pass through the column to elute [$^{18}$F] CDP2230.

The amount of radioactivity of the eluent obtained in Step 3 was 18.2 MBq (45 minutes after the start of synthesis). When TLC analysis was performed under the following conditions, the radiochemical purity was 97.5%. Further, when HPLC analysis was performed under the following conditions, the precursor compound 1 was not detected, but it was detected that non-radioactive impurities in an amount of 1.94 mg as converted into the precursor compound 1 were mixed.

(TLC Conditions)

Plate: TLC glass plate Silica gel $60F_{254}$

Developing solvent: acetonitrile/diethylamine/water=10:1:1

(HPLC Conditions)

Column: XBridge Phenyl (trade name, manufactured by Nippon Waters K.K, particle size: 3.5 µm, size: 4.6 mmφ× 100 mm)

Column temperature: constant temperature around 40° C.

Mobile phase: 10 mM ammonium hydrogen carbonate solution/methanol=50/50→35/65 (0→10 minutes), 35/65→0/100 (10→25 minutes)

Flow rate: 1.0 mL/min

Detector: UV-visible spectrophotometer (detection wave: 300 nm)

(Comparative Example 1) Preparation of [$^{18}$F] CDP2230

[$^{18}$F] CDP2230 was produced as follows in substantially the same manner as in Example 2, except that Step 2 of Example 2 was omitted.

[$^{18}$F] fluoride ion-containing $H_2^{18}O$ (with the amount of radioactivity being 34.9 MBq as a value corrected at the start of synthesis) was allowed to pass through Sep-Pak Light QMA (trade name, manufactured by Nihon Waters K.K.) prepared in carbonate type to adsorb and collect [$^{18}$F] fluoride ion. Subsequently, a tetraethylammonium bicarbonate aqueous solution (5.1 µmol/L, 0.2 mL) and a solution of 0.8 mL of acetonitrile were allowed to pass through the column to elute [$^{18}$F] fluoride ion. The resulting eluent was heated under argon gas flow at 110° C. to evaporate water. Thereafter, acetonitrile (0.3 mL×2) was added thereto, and the resulting mixture was azeotropically dried and solidified. 1.0 mL of a dimethyl sulfoxide solution in which 5 mg (equivalent to 9.52 µmol) of the precursor compound 1 was dissolved was added thereto, and the resulting mixture was heated at 100° C. for 7 minutes to perform a radiofluorination reaction.

After completion of the radiofluorination reaction, 15 mL of injection water was added to the reaction solution of the radiofluorination reaction, and allowed to pass through Oasis (registered trademark) WAX Plas (trade name, manufactured by Nihon Waters K.K.) to adsorb and collect [$^{18}$F] CDP2230 on the column. The column was washed with water (10 mL), and then ethanol (5 mL) was allowed to pass through the column to elute [$^{18}$F] CDP2230.

The amount of radioactivity of the obtained eluent was 13.4 MBq (46 minutes after the start of synthesis). When TLC analysis was performed under the conditions of Example 2, the radiochemical purity was 97.44%. Further, when HPLC analysis was performed under the conditions of Example 2, it was detected that 1.13 mg of the precursor compound 1 and 2.39 mg of non-radioactive impurities in total as converted into the precursor compound 1 were mixed.

(Example 3) Preparation of Radiofluorinated 1-(2,2-dihydroxymethyl-3-[$^{18}$F]fluoropropyl)-2-nitroimidazole Following Steps 1 to 4 below, 1-(2,2-dihydroxymethyl-3-[$^{18}$F]fluoropropyl)-2-nitroimidazole ($^{18}$F-labeled body of Compound 1 of WO 2013/042668), which is a hypoxic imaging agent, was produced.

Step 1: [$^{18}$F] fluoride ion-containing $H_2^{18}O$ (with the amount of radioactivity being 85.1 MBq as a value corrected at the start of synthesis) was allowed to pass through Sep-Pak Light QMA (trade name, manufactured by Nihon Waters K.K.) prepared in carbonate type to adsorb and collect [$^{18}$F] fluoride ion. Subsequently, a tetraethylammonium bicarbonate aqueous solution (5.1 µmol/L, 0.2 mL) and a solution of 0.8 mL of acetonitrile were allowed to pass through the column to elute [$^{18}$F] fluoride ion.

The resulting eluent was heated under argon gas flow at 110° C. to evaporate water. Thereafter, acetonitrile (0.3 mL×2) was added thereto, and the resulting mixture was azeotropically dried and solidified. 1.0 mL of a dimethyl sulfoxide solution in which 5 mg (equivalent to 11.7 µmol) of 2,2-dimethyl-5-[(2-nitro-1H-imidazol-1-yl) methyl]-5-(p-toluenesulfonyloxymethyl)-1,3-dioxane (precursor compound 2 corresponding to the product in Step 5 of FIG. 1 of WO 2013/042668) was dissolved was added thereto, and the resulting mixture was heated at 100° C. for 10 minutes to perform a radiofluorination reaction.

Step 2: After completion of Step 1, tetraethylammonium citrate (equivalent to 100 µmol) prepared in Example 1 was dissolved in 0.5 mL of dimethyl sulfoxide solution, added to the reaction solution of the radiofluorination reaction, and heated at 100° C. for 5 minutes.

Step 3: After completion of Step 2, 10 mL of injection water was added thereto, and the resulting mixture was allowed to pass through Oasis (registered trademark) WAX Plas (trade name, manufactured by Nihon Waters K.K.) to adsorb and collect a protected body of 1-(2,2-dihydroxymethyl-3-[$^{18}$F]fluoropropyl)-2-nitroimidazole on the column. After washing this column with water (10 mL), and then ethanol (3 mL) was allowed to pass through the column to elute the protected body of 1-(2,2-dihydroxymethyl-3-[$^{18}$F] fluoropropyl)-2-nitroimidazole.

Step 4: 2.0 mL of 1 mol/L hydrochloric acid was added to the eluent obtained in Step 3 and heated at 110° C. for 3 minutes for deprotection reaction. After reaction completion, 10 mL of injection water was added thereto, and the resulting mixture was allowed to pass through Oasis (registered trademark) HLB Plas (trade name, manufactured by Nihon Waters K.K.) to adsorb and collect 1-(2,2-dihydroxymethyl-3-[$^{18}$F] fluoropropyl)-2-nitroimidazole on the column. After washing this column with water (10 mL), and then ethanol (3 mL) was allowed to pass through the column to elute 1-(2,2-dihydroxymethyl-3-[$^{18}$F] fluoropropyl)-2-nitroimidazole.

The amount of radioactivity of the obtained eluent was 15.9 MBq (99 minutes after the start of synthesis). When TLC analysis was performed under the following conditions, the radiochemical purity was 98.84%. Further, when HPLC analysis was performed under the following conditions, it was confirmed that 0.91 mg of impurities derived from the precursor compound 2 and 1.27 mg of non-radioactive impurities in total as converted into the precursor compound 2 were mixed.

(TLC Conditions)
  Plate: TLC glass plate Silica gel 60F$_{254}$
  Developing solvent: ethyl acetate/methanol/triethylamine=5:1:0.5
(HPLC Conditions]
  Column: YMC-TriartC18 (trade name, manufactured by YMC, particle size: 5 μm, size: 4.6 mmφ×150 mm)
  Column temperature: constant temperature around 25° C.
  Mobile phase: 50 mM ammonium carbonate aqueous solution/acetonitrile=100/0→30/70 (0→40 minutes)
  Flow rate: 1.0 mL/min
  Detector: UV-visible spectrophotometer (detection wave: 254 nm)

(Comparative Example 2) Synthesis of Hypoxic Imaging Agent 1-(2,2-dihydroxymethyl-3-[$^{18}$F] fluoropropyl)-2-nitroimidazole was produced as follows in substantially the same manner as in Example 3, except that Step 2 of Example 3 was omitted.

[$^{18}$F] fluoride ion-containing H$_2$$^{18}$O (with the amount of radioactivity being 51.6 MBq as a value corrected at the start of synthesis) was allowed to pass through Sep-Pak Light QMA (trade name, manufactured by Nihon Waters K.K.) prepared in carbonate type to adsorb and collect [$^{18}$F] fluoride ion. Subsequently, a tetraethylammonium bicarbonate aqueous solution (5.1 μmol/L, 0.2 mL) and a solution of 0.8 mL of acetonitrile were allowed to pass through the column to elute [$^{18}$F] fluoride ion. The resulting eluent was heated under argon gas flow at 110° C. to evaporate water. Thereafter, acetonitrile (0.3 mL×2) was added thereto, and the resulting mixture was azeotropically dried and solidified. 1.0 mL of a dimethyl sulfoxide solution in which 5 mg (equivalent to 11.4 μmol) of the precursor compound 2 was dissolved was added, and the resulting mixture was heated at 100° C. for 7 minutes to perform a radiofluorination reaction.

After completion of the radiofluorination reaction, 10 mL of injection water was added to the reaction solution of the radiofluorination reaction, and the resulting mixture was allowed to pass through Oasis (registered trademark) WAX Plas (trade name, manufactured by Nihon Waters K.K.) to adsorb and collect a protected body of 1-(2,2-dihydroxymethyl-3-[$^{18}$F] fluoropropyl)-2-nitroimidazole on the column. After washing this column with water (10 mL), ethanol (3 mL) was allowed to pass through the column to elute the protected body of 1-(2,2-dihydroxymethyl-3-[$^{18}$F] fluoropropyl)-2-nitroimidazole.

2.0 mL of 1 mol/L hydrochloric acid was added to this eluent, and heated at 110° C. for 3 minutes. After reaction completion, 10 mL of injection water was added thereto, and the resulting mixture was allowed to pass through Oasis (registered trademark) HLB Plas (trade name, manufactured by Nihon Waters K.K.) to adsorb and collect 1-(2,2-dihydroxymethyl-3-[$^{18}$F] fluoropropyl)-2-nitroimidazole on the column. After washing this column with water (10 mL), ethanol (3 mL) was allowed to pass through the column to elute 1-(2,2-dihydroxymethyl-3-[$^{18}$F] fluoropropyl)-2-nitroimidazole.

The amount of radioactivity of the obtained eluent was 13.2 MBq (90 minutes after the start of synthesis). When TLC analysis was performed under the conditions of Example 3, the radiochemical purity was 98.00%. Further, when HPLC analysis was performed under the conditions of Example 3, it was confirmed that 2.23 mg of impurities derived from the precursor compound 2 and 2.27 mg of non-radioactive impurities as converted into the precursor compound 2 were mixed.

From the above examples, it is suggested that, according to the method of the present invention, the reaction product of the radiohalogenation reaction can be separated and purified from the unreacted radiohalogen-labeling precursor compound by the solid phase extraction method without depending on the conventional HPLC method.

This application claims priority based on Japanese Patent Application No. 2017-122981 filed on Jun. 23, 2017, the entire disclosure of which is incorporated herein.

The invention claimed is:

1. A method for producing a radiohalogen-labeled compound, the method comprising:
   a step of performing a radiohalogenation reaction on a radiohalogen-labeling precursor compound having a leaving group capable of being nucleophilically substituted by a radioactive halide ion for obtaining a first reaction mixture containing the radiohalogen-labeling precursor compound and a reaction product of the radiohalogenation reaction;
   a step of performing a substitution reaction between the leaving group of the radiohalogen-labeling precursor compound and a polyvalent acid or a salt thereof, by mixing the first reaction mixture with the polyvalent acid or salt thereof, for obtaining a second reaction mixture; and
   a step of purifying the reaction product from the second reaction mixture by a solid phase extraction method in which a solid phase cartridge having an anion exchange group is used,
   wherein the radiohalogen is radioactive fluorine,
   the leaving group is a sulfonyloxy group which is selected from the group consisting of an aromatic sulfonyloxy group and an alkylsulfonyloxy group, and
   the polyvalent acid is a polyvalent organic acid having a plurality of acidic groups which are each selected from the group consisting of a carboxyl group and a phenol group or are a combination of these acidic groups.

2. The method for producing a radiohalogen-labeled compound according to claim 1, wherein the step for obtaining the second reaction mixture includes mixing the first reaction mixture with the polyvalent acid or the salt thereof, and then heating the mixture for obtaining the second reaction mixture.

3. The method for producing a radiohalogen-labeled compound according to claim 1, wherein the salt of the polyvalent acid is a salt formed of the polyvalent acid and a phase transfer catalyst.

4. A method for producing a radiopharmaceutical containing a radiohalogen-labeled compound as an active ingredient, the method comprising:
   carrying out the method for producing a radiohalogen-labeled compound according to claim 1, and
   adding a pH regulator, a solubilizer, a stabilizer, or an antioxidant to the produced radiohalogen-labeled compound.

* * * * *